(12) United States Patent
Toda et al.

(10) Patent No.: US 9,700,464 B2
(45) Date of Patent: Jul. 11, 2017

(54) ABSORBENT ARTICLE

(75) Inventors: Haruki Toda, Kagawa (JP); Kaiyou Nakajima, Kagawa (JP)

(73) Assignee: Unicharm Corporation, Ehime (JP)

( * ) Notice: Subject to any disclaimer, the term of this patent is extended or adjusted under 35 U.S.C. 154(b) by 195 days.

(21) Appl. No.: 13/988,381

(22) PCT Filed: Nov. 14, 2011

(86) PCT No.: PCT/JP2011/076613
§ 371 (c)(1),
(2), (4) Date: May 20, 2013

(87) PCT Pub. No.: WO2012/067216
PCT Pub. Date: May 24, 2012

(65) Prior Publication Data
US 2013/0245589 A1  Sep. 19, 2013

(30) Foreign Application Priority Data
Nov. 19, 2010  (JP) .................................. 2010-259340

(51) Int. Cl.
*A61F 13/15* (2006.01)
*A61F 13/51* (2006.01)
(Continued)

(52) U.S. Cl.
CPC ............ *A61F 13/51* (2013.01); *A61F 13/495* (2013.01); *A61F 13/4942* (2013.01);
(Continued)

(58) Field of Classification Search
CPC ...... A61F 2013/530868; A61F 13/5323; A61F 13/532; A61F 13/533
(Continued)

(56) References Cited

U.S. PATENT DOCUMENTS

| 4,834,735 A | 5/1989 | Alemany et al. |
|---|---|---|
| 5,494,622 A | 2/1996 | Heath et al. |

(Continued)

FOREIGN PATENT DOCUMENTS

| EP | 0 689 815 A1 | 1/1996 |
|---|---|---|
| JP | H01-282301 A | 11/1989 |

(Continued)

OTHER PUBLICATIONS

International Search Report based on corresponding PCT application No. PCT/JP2011/076613 dated Jan. 17, 2012 (2 pgs).

(Continued)

*Primary Examiner* — Jacqueline Stephens
(74) *Attorney, Agent, or Firm* — Brinks Gilson & Lione

(57) ABSTRACT

An absorbent article which has in a longitudinal direction from the front side to the rear side a front waist region, a rear waist region and a crotch region located between the front and rear waist regions. An absorbent sheet is provided between a topsheet and a second sheet which includes at least one liquid-pervious sheet having sandwiched therein an absorbent polymer that is present between a topsheet and a second sheet. The second sheet has a higher liquid diffusibility than the topsheet, the topsheet, a backsheet, an absorption body and the second sheet are disposed across the front waist region, the crotch region and the rear waist region, and the absorbent sheet is disposed in at least a part of the rear waist region.

21 Claims, 7 Drawing Sheets

(51) Int. Cl.

| | |
|---|---|
| *A61F 13/494* | (2006.01) |
| *A61F 13/495* | (2006.01) |
| *A61F 13/537* | (2006.01) |
| *A61F 13/539* | (2006.01) |
| *A61F 13/532* | (2006.01) |
| *A61F 13/533* | (2006.01) |
| *A61F 13/53* | (2006.01) |
| *A61F 13/84* | (2006.01) |

(52) U.S. Cl.
CPC .... *A61F 13/4946* (2013.01); *A61F 13/49473* (2013.01); *A61F 13/539* (2013.01); *A61F 13/53717* (2013.01); *A61F 13/53747* (2013.01); *A61F 13/532* (2013.01); *A61F 13/533* (2013.01); *A61F 13/5323* (2013.01); *A61F 2013/530554* (2013.01); *A61F 2013/530562* (2013.01); *A61F 2013/530868* (2013.01); *A61F 2013/8497* (2013.01)

(58) Field of Classification Search
USPC ............ 604/378, 385.01, 385.101, 379
See application file for complete search history.

(56) References Cited

U.S. PATENT DOCUMENTS

| | | | |
|---|---|---|---|
| 5,593,399 A | | 1/1997 | Tanzer et al. |
| 5,873,867 A | * | 2/1999 | Coles ............... A61F 13/15203 |
| | | | 604/368 |
| 2006/0184146 A1 | | 8/2006 | Suzuki |
| 2007/0093164 A1 | | 4/2007 | Nakaoka |

FOREIGN PATENT DOCUMENTS

| | | |
|---|---|---|
| JP | 2003-93441 A | 4/2003 |
| JP | 2004-275225 A | 10/2004 |
| JP | 2004-329664 A | 11/2004 |
| JP | 2005-6954 A | 1/2005 |
| JP | 2008-284190 A | 11/2008 |
| JP | 2009-028186 A | 2/2009 |

OTHER PUBLICATIONS

European extended Search Report from corresponding European Application No. 1184382.1 dated Mar. 5, 2014 (5 pgs).

\* cited by examiner

ABSORBENT ARTICLE

RELATED APPLICATION

This application is a 35 U.S.C. §371 national phase filing of International Patent Application No. PCT/JP2011/076613, filed Nov. 14, 2011, through which and to which priority is claimed under 35 U.S.C. §119 to Japanese Patent Application No. 2010-259340, filed Nov. 19, 2010.

TECHNICAL FIELD

The present invention relates to an absorbent article. More specifically, the present invention relates to an absorbent article such as urine-absorbing pad, disposable diaper, toilet training pant and incontinence brief.

BACKGROUND ART

An absorbent article comprising an absorption body, a topsheet disposed to cover the front surface of the absorption body and at least partially composed of a liquid-pervious material, and a backsheet disposed on the back surface of the absorption body and composed of a liquid-impervious material, wherein the absorption body has a hole part formed to extend from the front surface to the back surface of the absorption body at least in a region corresponding to the wearer's excretory site (excretory region), a diffusion sheet is disposed on the back surface of the absorption body to cover the opening of the hole part at least in the excretory region while arranging the topsheet on the front surface of the absorption body, and a water-repellent sheet is disposed in a region above the diffusion sheet, which is located behind the excretory region when wearing, is known as a conventional technique (see, for example, Patent Literature 1).

This absorbent article is not only excellent in the absorptivity of a liquid excrement but also can effectively prevent a return of the liquid excrement. That is, in the absorbent article above, a liquid excrement is absorbed at the excretory site in the topsheet side surface (front surface) of the absorption body and at the same time, the liquid excrement is partially allowed to pass through the hole part and permeate the diffusion sheet, whereby the liquid excrement can be absorbed from the back surface of the absorption body by way of the diffusion sheet. In this way, since liquid excrement can be absorbed in a wider region, the liquid excrement can be absorbed at a high absorption rate with excellent absorptivity. Also, the absorption body comprises a water-repellent sheet disposed in a region above the diffusion sheet, which is located behind the excretory region on wearing, so that in the buttock region where a body pressure is readily imposed during wearing and liquid excrement is liable to cause a return, the liquid excrement can be restricted from seeping to the absorption body surface and return of the liquid excrement can be effectively prevented.

CITATION LIST

Patent Literature

[Patent Literature 1] Kokai (Japanese Unexamined Patent Publication) No. 2009-28186

SUMMARY OF THE INVENTION

Technical Problem

However, the conventional absorbent article described in Patent Document 1 sometimes faces a problem that when the wearer's urination orifice is not contacted with the absorbent article, the excreted urine diffuses by running down the wearer's skin, as a result, the urine is spread on the water-repellent sheet in the rear part and the skin remains wetted with urine.

Solution to Problem

In order to solve the problem above, the present invention employs the following configuration.

That is, the present invention is an absorbent article consisting of a front waist region, a rear waist region and a crotch region located between the front and rear regions in a longitudinal direction from a front side to a rear side, comprising a liquid-pervious topsheet, a backsheet, an absorption body intervening between the topsheet and the second sheet, a second sheet disposed between the absorption body and the topsheet, and an absorbent sheet between the topsheet and the second sheet, comprising at least one liquid-pervious sheet having sandwiched thereby an absorbent polymer, wherein: the second sheet is higher in the liquid diffusibility than the topsheet; the topsheet, the backsheet, the absorption body and the second sheet are disposed across the front waist region, the crotch region and the rear waist region; and the absorbent sheet is disposed in at least a part of the rear waist region.

Advantageous Effects of the Invention

According to the present invention, even when the excreted urine diffuses by running down the wearer's skin, the skin of buttocks is prevented from remaining wetted with urine, i.e., the wearer's skin can be kept in a dry, comfortable state.

DESCRIPTION OF EMBODIMENTS

Figure 1:
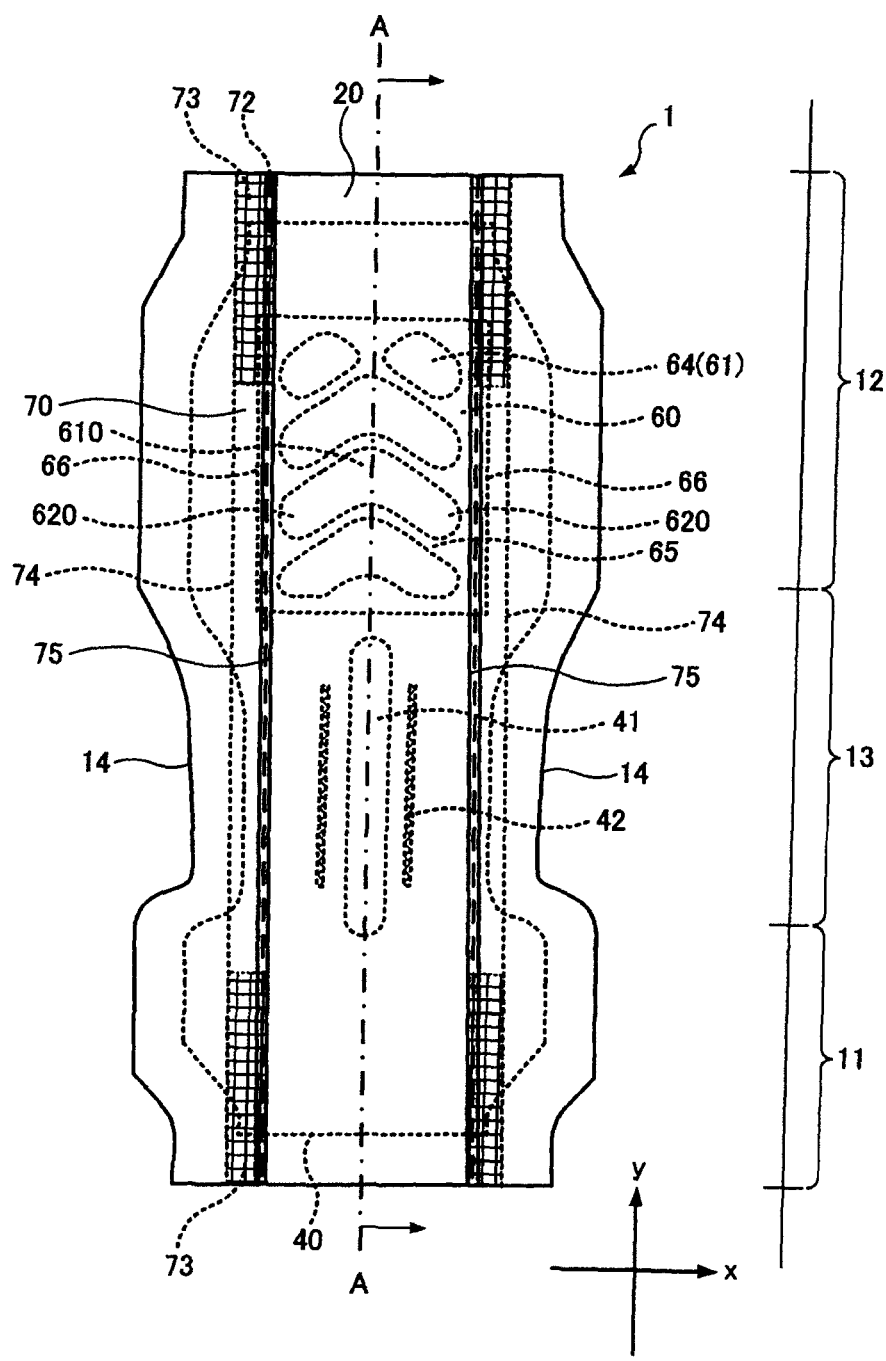
FIG. 1 is a plan view of the absorbent article according to one embodiment of the present invention when viewed from the wearer's skin side.

The absorbent article according to one embodiment of the present invention is described below by referring to the drawings. The absorbent article according to one embodiment of the present invention is a urine-absorbing pad.

Figure 2:
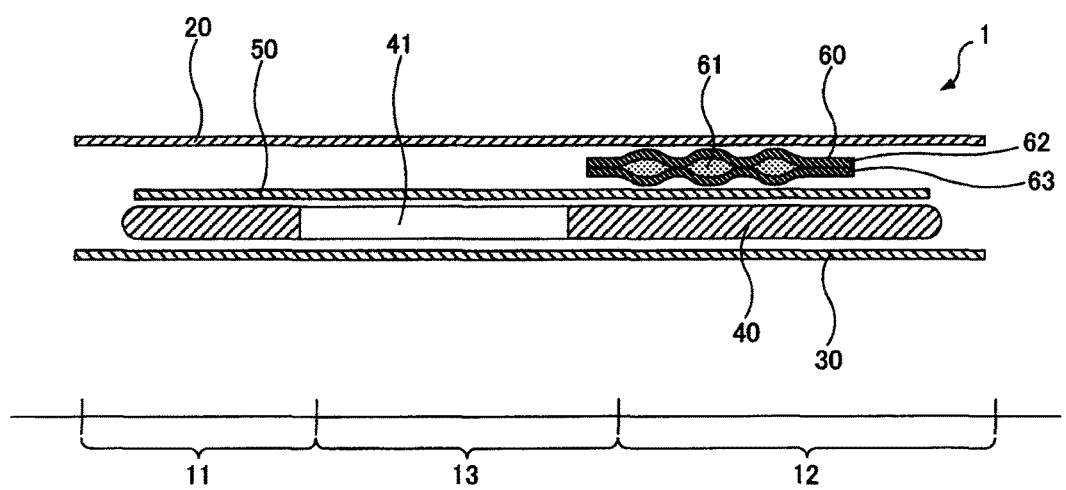
FIG. 2 is a schematic view of the A-A cross-section of FIG. 1.
Figure 3:
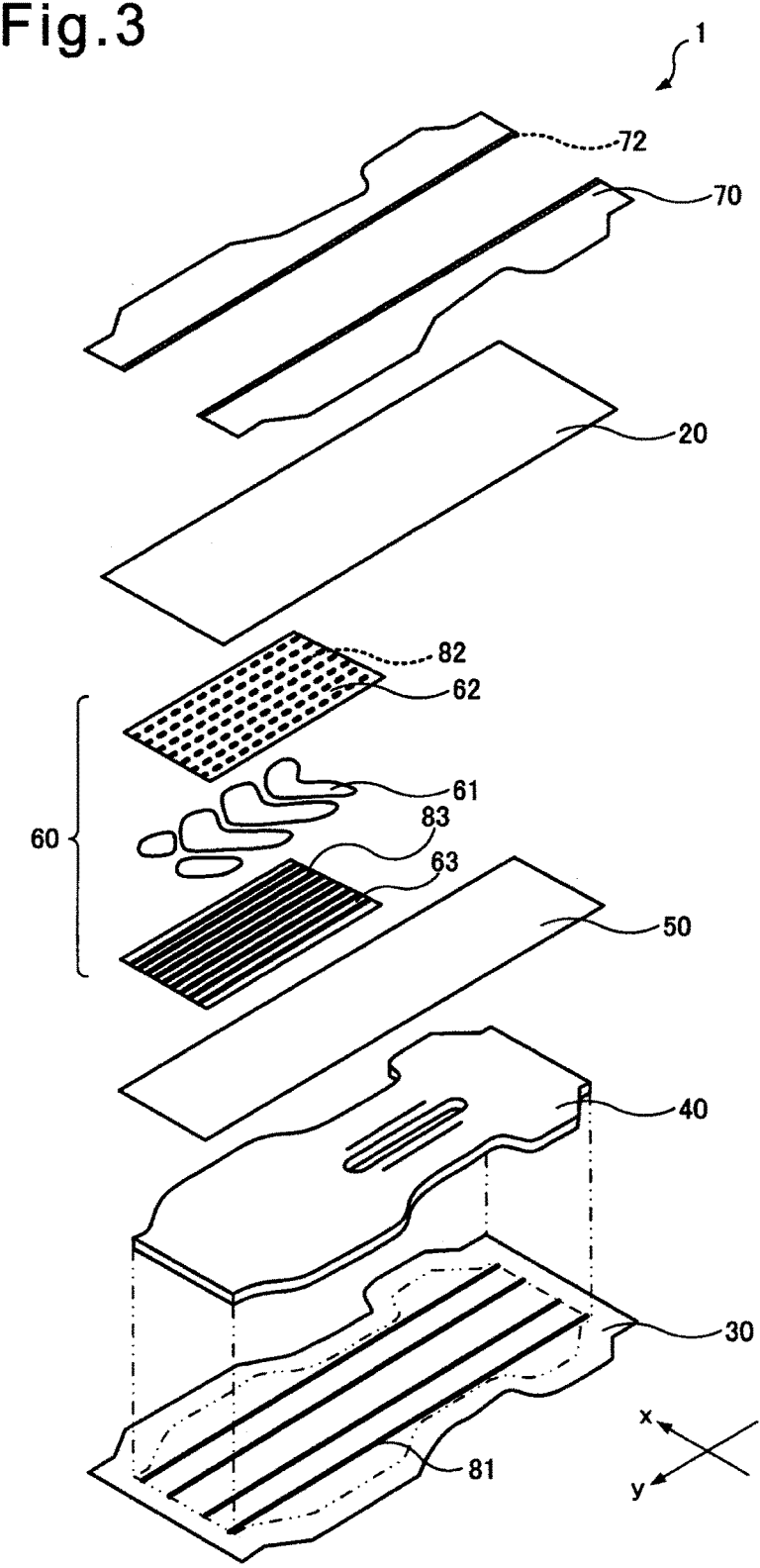
FIG. 3 is an exploded view of the absorbent article according to one embodiment of the present invention.
Figure 4:
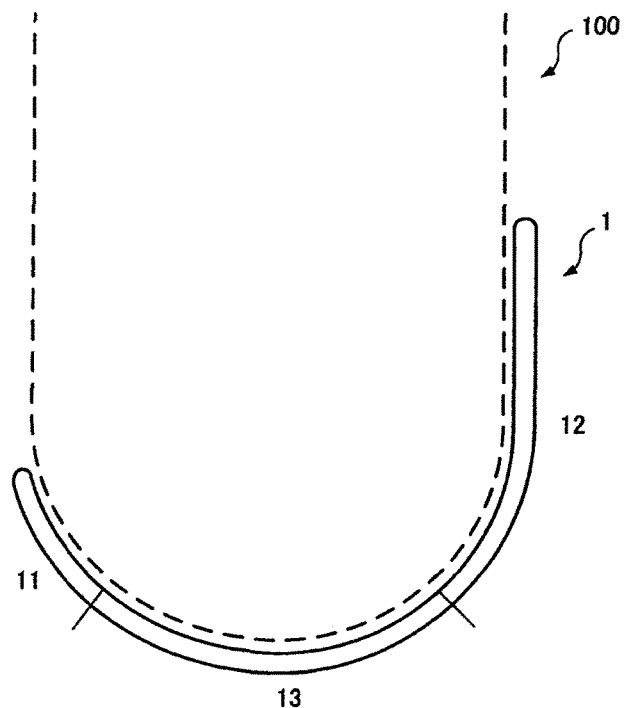
FIG. 4 is a view showing the worn state of the absorbent article according to one embodiment of the present invention.

FIG. 1 is a plan view of the absorbent article according to one embodiment of the present invention when viewed from the wearer's skin side, FIG. 2 is a schematic view of the A-A cross-section of FIG. 1, FIG. 3 is an exploded view of the absorbent article according to one embodiment of the present invention, and FIG. 4 is a view showing the worn state of the absorbent article according to one embodiment of the present invention. The x-axis direction shown in the Figures is the width direction of the absorbent article 1, the y-axis direction is the longitudinal direction of the absorbent article 1, and the xy direction is the planar direction of the absorbent article 1.

As shown in FIG. 1, the absorbent article 1 is divided into a front waist region 11, a rear waist region 12, and a crotch region 13 between the front waist region 11 and the rear waist region 12. The front waist region 11 side of the absorbent article 1 is referred to as the front side and the rear waist region 12 side of the absorbent article 1 is referred to as the rear side. As shown in FIG. 4, the crotch region 13 is a region applied to the crotch of a wearer 100 when the absorbent article is worn, the front waist region 11 is a region on the front side relative to the crotch region 13, and the rear waist region 12 is a region on the rear side relative to the crotch region 13. In the crotch region 13, the side part 14 is bent or curved to decrease the dimension in the width direction of the absorbent article 1. The "crotch part" as used herein indicates the region between both femoral areas of the wearer when the wearer stands erect. Accordingly, the front waist region 11 covers the belly side of the wearer, and the rear waist region 12 covers the buttocks of the wearer. That is, the crotch region 13 is a region applied to the wearer's crotch part, the front waist region 11 is a region covering the front side relative to the wearer's crotch, and the rear waist region 12 is a region covering the rear side relative to the wearer's crotch part.

The absorbent article 1 in one embodiment of the present invention comprises a liquid-pervious topsheet 20, a backsheet 30 provided at the position opposing the topsheet 20, and an absorption body 40 provided between the topsheet 20 and the backsheet 30. A second sheet 50 is disposed between the topsheet 20 and the absorption body 40, and an absorbent sheet 60 is disposed between the topsheet 20 and the second sheet 50. On both widthwise sides of the absorbent article 1, a leak-preventive cuff 70 is disposed.

The topsheet 20 is a liquid-pervious sheet that allows excreted urine to permeate therethrough and is provided on the surface coming into contact with the wearer's skin when the wearer wears the absorbent article 1. Accordingly, the topsheet 20 preferably has a function of giving a soft and comfortable touch to skin. For example, the topsheet 20 may be produced using a fine fiber and have smooth surface and large latitude for deformation. Generally, a nonwoven fabric is used for the topsheet 20. Examples of the nonwoven fabric used for the topsheet 20 include a spunbond nonwoven fabric, a point bond nonwoven fabric and an air-through nonwoven fabric. The topsheet 20 is disposed across the front waist region 11, the crotch region 13 and the rear waist region 12.

The backsheet 30 is a liquid-impervious sheet that does not allow permeation of urine and is provided to prevent the excreted urine from leaking outside. The material of the backsheet 30 is not particularly limited as long as it is a material allowing no permeation of excreted urine. For example, a waterproof-treated nonwoven fabric, a plastic film composed of polyethylene or the like, or a composite material of nonwoven fabric and plastic film can be used for the backsheet 30. Also, in order to prevent the absorbent article 1 in wearing from causing stuffiness due to exhalation of water vapor through the backsheet 30, a breathable film may be used for the backsheet 30. Incidentally, in the case of a urine-absorbing pad or the like used inside a diaper, the backsheet need not be liquid-impervious. The backsheet 30 is disposed across the front waist region 11, the crotch region 13 and the rear waist region 12.

The absorption body 40 has a function of absorbing and holding excreted urine. The absorption body 40 includes, for example, an absorption body composed of a fluffed pulp or an air-laid nonwoven fabric and a super-absorbent polymer (SAP). The absorption body 40 can alternatively includes, for example, a chemical pulp, a cellulose fiber, an artificial cellulose fiber such as rayon and acetate, or a fiber network absorption body using a synthetic fiber (including a composite fiber) such as polyolefin, polyester and polyamide, or can be a foam absorption body using a foam material such as polyurethane, instead of using a fluffed pulp.

The absorption body 40 has nearly similar in shape to the backsheet 30 and the size of the absorption body 40 is small compared with the backsheet 30. The absorption body 40 is disposed across the front waist region 11, the crotch region 13 and the rear waist region 12. The absorption body 40 has a penetration part 41 and a compressed grooves 42. The penetration part 41 may be a hole penetrating the absorption body 40 in the thickness direction and at the widthwise central position of the absorption body 40. The penetration part 41 longitudinally extends across the crotch region 13 up to or into the front waist region 11. However, the penetration part 41 is kept from longitudinally extending to a position that would cause it to overlap with the absorbent sheet 60 in the thickness direction. That is, the projection image of the penetration part 41 when the penetration part 41 is projected in the thickness direction of the absorbent article 1 does not overlap with the projection image of the absorbent sheet 61 when the absorbent sheet 60 is projected in the thickness direction of the absorbent article 1. The compressed grooves 42 are disposed on both sides of the penetration part 41 to align with each other and are grooves that longitudinally extend across the crotch region 13 and are dented from the topsheet side surface of the absorption body 40. The longitudinal length of the compressed grooves 42 is short compared with the longitudinal length of the penetration part 41. The compressed grooves 42 are formed by heating•pressurizing the absorption body 40 toward the backsheet 30 side surface from the topsheet 20 side surface of the absorption body 40. The absorption body 40 is adhered to the backsheet 30 by a hot-melt adhesive (HMA) 81. The absorption body 40 may have a rectangular, oval or other shape instead of having a nearly similar figure to the backsheet 30.

The second sheet 50 is a sheet for planarly diffusing the urine permeated through a partial region of the topsheet 20. Thanks to this sheet, the absorption body 40 can absorb the urine permeated through a partial region of the topsheet 20, in a wide region on the topsheet 20 side surface of the absorption body 40. The second sheet 50 is disposed across the front waist region 11, the crotch region 13 and the rear waist region 12.

For the second sheet 50, a nonwoven fabric having high liquid diffusibility, such as tissue, point bond nonwoven fabric and rayon-containing spun lace nonwoven fabric, is preferably used. In particular, the liquid diffusibility of the second sheet 50 is preferably higher than the liquid diffusibility of the topsheet 20. For example, in the case of using a spunbond nonwoven fabric for the topsheet 20, a tissue, a point bond nonwoven fabric, a spun lace nonwoven fabric (particularly, rayon-containing), which are higher in the liquid diffusibility than the spun bond nonwoven fabric, or a mixture thereof is preferably used for the second sheet 50.

The liquid diffusibility of the sheet can be evaluated, for example, by the Klemm water absorbency of the sheet measured in accordance with JIS P8141 "Paper and Paperboard—Water Absorbency Test Method—Klemm Method", since paper is a kind of nonwoven fabric. The Klemm water absorbency is a height to which water rises in 10 minutes due to a capillary phenomenon when the lower end of a specimen is vertically dipped in water, and a higher Klemm water absorbency of the sheet indicates higher diffusibility of the sheet. For example, the Klemm water absorbency of a tissue having a basis weight of 15 g/m$^2$ was 28 mm, the Klemm water absorbency of a spun lace nonwoven fabric (rayon-containing) having a basis weight of 38 g/m$^2$ was 118 mm, the Klemm water absorbency of a point bond nonwoven fabric having a basis weight of 23 g/m$^2$ was 36 mm, the Klemm water absorbency of an air-through nonwoven fabric having a basis weight of 25 g/m$^2$ was 3 mm, and the Klemm water absorbency of a spunbond nonwoven fabric having a basis weight of 20 g/m$^2$ was 2 mm. Accordingly, among these nonwoven fabrics, a spun lace nonwoven fabric (rayon-containing) having a highest Klemm water absorbency is most preferred as the sheet used for the second sheet 50, and a tissue and a point bond nonwoven fabric each having a high Klemm water absorbency are also preferred. However, an air-through nonwoven fabric and a spunbond nonwoven fabric each having a low Klemm water absorbency are not as preferred as the sheet used for the second sheet 50. Generally, the Klemm water absorbency is higher as the density of the nonwoven fabric is higher, and is more increased when the nonwoven fabric contains a water-absorbent fiber such as rayon.

The absorbent sheet 60 is a composite sheet where an absorbent polymer 61 is sandwiched between two liquid-pervious sheets 62 and 63. For example, a nonwoven fabric is used for the liquid-pervious sheets 62 and 63. Incidentally, the absorbent sheet may be produced by sandwiching an absorbent polymer by three or more liquid-pervious sheets. Also, the absorbent sheet may be produced by sandwiching an absorbent polymer by a folded liquid-pervious sheet. That is to say, the absorbent sheet is produced by sandwiching an absorbent polymer by at least one liquid-pervious sheet. The absorbent polymer is a polymer capable of absorbing water and is, for example, an absorbent macromolecular polymer having a three-dimensional network structure formed by appropriate crosslinking of water-soluble macromolecules. Such an absorbent macromolecular polymer absorbs several hundreds or thousands of times as much water as the volume before absorbing water but is substantially water-insoluble and does not release the once absorbed water even when some pressure is applied. Examples of the absorbent polymer include starch-based, acrylic acid-based or amino acid-based particulate or fibrous polymers. An absorbent polymer 61 is sandwiched by two liquid-pervious sheets 62 and 63 and then, these two liquid-pervious sheets 62 and 63 are joined, whereby the absorbent sheet 60 is produced. Accordingly, in order to prevent the absorbent polymer from spilling after sandwiching the absorbent polymer 61 between two liquid-pervious sheets 62 and 63, the particle diameter of the absorbent polymer is preferably large compared with the fiber interstices of the liquid-pervious sheets 62 and 63. For example, a spunbond nonwoven fabric, a point bond nonwoven fabric, an air-through nonwoven fabric or an SMS (spunbond-melt blown-spunbond) nonwoven fabric may be used for the liquid-pervious sheets 62 and 63. The liquid-pervious sheets 62 and 63 must have permeability to urine and therefore, they are preferably subjected to a hydrophilization treatment.

On the absorbent polymer 61-sandwiching surfaces of the liquid-pervious sheets 62 and 63, a plurality of longitudinally extending adhesive parts 82 and 83 aligned in the width direction are provided. Incidentally, the adhesive parts 82, 83 may be provided on the absorbent polymer 61-sandwiching surface of one liquid-pervious sheet 62 and 63 out of the liquid-pervious sheets 62 and 63. The adhesive part 82 and 83 is formed, for example, by coating a hot-melt adhesive in a streak manner. Thanks to this adhesive, the absorbent polymer 61 is fixed to the liquid-pervious sheets 62 and 63. The coating method is not limited to the streaky coating method as long as it is a coating method capable of providing a region absent of the adhesive part, for example, intermittently disposing the adhesive part, since permeability of urine in the adhesive part 82 and 83 is poor. A non-contact coating method such as omega patterned coating may be also employed. The adhesive part 82 and 83 is intermittently provided in the later-described absorbent polymer-existing region 64, so that the absorbent polymer 61 can be prevented from being biased in the absorbent polymer-existing region 64. The adhesive part-to-adhesive part distance between adjacent adhesive parts of the adhesive parts 83 provided on the liquid-pervious sheet 63 on the second sheet 50 side is small compared with the adhesive part-to-adhesive part distance of the adhesive parts 82 provided on the liquid-pervious sheet 62 on the topsheet 20 side. Thanks to this configuration, the excreted urine can easily pass between the adhesive parts 82 through the liquid-pervious sheet 62, and the absorbent polymer 61 is evenly fixed to the liquid-pervious sheet 63 on the second sheet 50 side.

When streaky adhesive parts 82 colored blue or the like are provided on the liquid-pervious sheets 62 and 63, a striped pattern with blue or the like color is imparted to the absorbent article 1 and in turn, the appearance of the absorbent article 1 is improved. Incidentally, the adhesive part 82 may be provided only on the absorbent polymer 61-sandwiching surface of the liquid-pervious sheet 63 on the second sheet 50 side. By providing the adhesive part 82 on the liquid-pervious sheets 62 and/or 63, the absorbent polymer 61 can be kept from moving in the absorbent sheet 60 before the absorbent polymer 61 swells.

The absorbent sheet 60 is preferably disposed in at least a part of the rear waist region 12. Thanks to this configuration, when the wearer's urination orifice is contacted with the absorbent article 1, the urine excreted without permeating through the absorbent sheet 60 can be directly absorbed by the absorption body 40, and when the wearer's urination orifice is not contacted with the absorbent article 1, the urine can be absorbed by the absorbent sheet 60.

In the absorbent sheet 60, the absorbent polymer 61 is disposed in parts in a plurality of regions 64 (hereinafter, referred to as an "absorbent polymer-existing region"), and a region 65 having not disposed therein the absorbent polymer 61 (hereinafter, referred to as an "absorbent polymer-nonexisting region") is provided between respective absorbent polymer-existing regions 64. Thanks to this configuration, even when the absorbent polymer 61 in the absorbent polymer-existing region 64 fully swells by absorbing urine and cannot absorb urine any more, the urine passes through the absorbent polymer-nonexisting region 65 and is absorbed by the absorption body 40. Incidentally, in an absorbent article that is not continuously used until the absorbent polymer fully swells, the absorbent polymer-nonexisting region need not be provided in the absorbent sheet.

The widthwise central portion 610 in the absorbent polymer-existing region 64 is located on the rear side in a direction towards the edge of the rear waist region, compared with each of widthwise outward portions 620 relative to the widthwise central portion 610 in the absorbent polymer-existing region 64. Thanks to this configuration, when the wearer's urination orifice is contacted with the absorbent article 1, the excreted urine can be directly absorbed by the absorption body 40 without being absorbed by the absorbent polymer 61 in the absorbent polymer-existing region 64, and when the wearer's urination orifice is not contacted with the absorbent article 1, the urine can be absorbed by the absorbent polymer 61 in the absorbent polymer-existing region 64.

The planar shape of the absorbent polymer-existing region 64 is a nearly V-shape projecting in the direction from the front waist region 11 to the rear waist region 12 in the longitudinal direction of the absorbent article 1 and extending in the width direction of the absorbent article 1. That is, the planar shape of the absorbent polymer-existing region 64 is a nearly V-shape with the apex facing in the direction from the front waist region 11 to the rear waist region 12 in the longitudinal direction of the absorbent article 1. However, the absorbent polymer-existing region 64 most remote from the front waist region 11 may have a shape formed by cutting out the widthwise center of the nearly V-shape or nearly circular arc shape to divide it into two regions. Since the nearly V-shape of the absorbent polymer-existing region 64 is a shape following the wearer's buttocks, the absorbent polymer-existing region 64 fits over the wearer's buttocks and a gap is scarcely produced between the wearer and the absorbent article 1. Incidentally, the shape of the absorbent polymer-existing region is not limited to the nearly V-shape as long as an absorbent polymer-nonexisting region is present. For example, the shape of the absorbent polymer-existing region may be a circular arc shape, a round shape, a rectangular shape or a triangular shape.

As described above, the absorbent sheet 60 is produced by sandwiching an absorbent polymer 61 by two liquid-pervious sheets 62 and 63 and then, joining these two liquid-pervious sheets 62 and 63. Accordingly, the region where the absorbent polymer 61 is sandwiched between two liquid-pervious sheets 62 and 63 is the absorbent polymer-existing region 64, and the region where two liquid-pervious sheets 62 and 63 are joined without sandwiching the absorbent polymer 61 between those two liquid-pervious sheets 62 and 63 is the absorbent polymer-nonexisting region 65. Joining of these two liquid-pervious sheets 62 and 63 requires strength high enough to withstand the expansion force due to swelling of the absorbent polymer 61. Otherwise, two liquid-pervious sheets 62 and 63 can become separated from each other due to swelling of the absorbent polymer 61 to produce a gap between the two liquid-pervious sheets 62 and 63 and allow intrusion of the absorbent polymer 61 into the gap, resulting in disappearance of the absorbent polymer-nonexisting region 65. For joining the liquid-pervious sheets 62 and 63 with a desired strength, a heat seal, a sonic seal, an adhesive or the like can be used.

In the case of joining the liquid-pervious sheets 62 and 63 with each other by a heat seal, when the linear pressure in the width direction of the heat seal is constant, uniform seal strength is achieved in whole. For this reason, the linear pressure in the width direction of the heat seal is preferably constant. For keeping a uniform linear pressure in the width direction of the heat seal, the total of the widthwise lengths of regions to be sealed must be made constant. For example, as described above, absorbent polymer-existing regions 64 are formed in a nearly V-shape or a nearly circular arc shape and aligned in the longitudinal direction, whereby the total of the widthwise lengths of the absorbent polymer-nonexisting regions 65 can be made substantially constant. In the case of joining the liquid-pervious sheets 62 and 63 with each other by using an adhesive, the adhesive is preferably of a type capable of exerting the strength even when wetted, because the liquid-pervious sheets 62 and 63 are in a wet state when the absorbent polymer 61 is swelled.

The absorbent polymer 61 swells once absorbing urine and therefore, in the absorbent polymer-existing region 64, the absorbent polymer 61 preferably reserves, between two liquid-pervious sheets 62 and 63, a volume large enough to enable fully swelling of the absorbent polymer 61. If the absorbent polymer 61 is densely packed too much between two liquid-pervious sheets 62 and 63, the absorbent polymer 61 cannot be completely swelled and in turn, the absorption ability of the absorbent polymer 61 may not be sufficiently utilized.

When the number of absorbent polymer-existing regions 64 in the absorbent sheet 60 is increased, the area of the absorbent polymer-nonexisting region 65 is increased, but the total amount by volume of the absorbent polymer 61 in the absorbent sheet 60 decreases and therefore, the amount of urine that can be absorbed by the absorbent sheet 60 becomes small. On the other hand, when the number of absorbent polymer-existing regions 64 in the absorbent sheet 60 is decreased, the total amount by volume of the absorbent polymer 61 in the absorbent sheet 60 is increased and the amount of urine that can be absorbed by the absorbent sheet 60 becomes large, but the area of the absorbent polymer-nonexisting region 65 decreases and it may not occur that after the absorbent polymer is swelled, urine permeates through the absorbent sheet 60 and is absorbed by the absorption body 40. Accordingly, the number of absorbent polymer-existing regions 64 need to be selected by considering the balance between the amount of urine that can be absorbed by the absorbent sheet 60 and the permeability to urine of the absorbent sheet 60 after the absorbent polymer 61 is swelled and by further considering the volume of the absorbent polymer 61 after swelling, which is dependent on the kind and charge amount of the polymer. For example, in the case of an absorbent sheet with a size of 180 mm×130 mm, 2 g of an absorbent polymer capable of absorbing 60 g of a normal saline solution per 1 g is disposed in parts in 5 absorbent polymer-existing regions, whereby an absorbent sheet well-balanced between the urine absorbability and permeability to urine after swelling of the absorbent polymer can be obtained. The percentage of the area of the absorbent polymer-existing regions 64 to the area of the absorbent sheet 60 preferably is 40 to 80%. When the percentage of the area of the absorbent polymer-existing regions 64 to the area of the absorbent sheet 60 is less than 40%, the urine absorbed by the absorption body 40 may wet the wearer's buttocks. When the percentage of the area of the absorbent polymer-existing regions 64 to the area of the absorbent sheet 60 is more than 80%, after the absorbent polymer is swelled, urine may not permeate through the absorbent sheet 60 and may not be absorbed by the absorption body 40.

The leak-preventive cuffs 70 prevent excreted urine from leaking outside at a widthwise positions of the absorbent article 1. In both widthwise side parts of the absorbent article 1, a longitudinally extending leak-preventive cuff 70 is disposed. A hydrophobic nonwoven fabric such as SMS nonwoven fabric is used for the leak-preventive cuffs 70. A leak-preventive material such as waterproof film may be also used in place of SMS nonwoven fabric. The leak-preventive cuffs 70 are joined with the topsheet 20 or the backsheet 30 in the widthwise side parts of the absorbent article 1 by using an adhesive and have a base end part 74 and a free end part 75. The base end parts 74 are joined with the widthwise side parts of the absorbent article 1 and can be fixed using a heat seal in place of an adhesive. The base end part 74 may be also located at the side edges or backsheet surface of the absorbent article 1. The free end parts 75 are located on the widthwise inner sides of the absorbent article 1 relative to the base end parts 74. An elastic body 72 capable of extending in the longitudinal direction and fixed in an extended state is provided in the vicinity of the free end parts 75 of the leak-preventive cuffs 70. Also, the regions 73 on the longitudinal end sides of the leak-preventive cuffs 70 are joined with the topsheet 20 by using an adhesive. When the elastic bodies 72 develop its contractive force, the free end parts 75 of the leak-preventive cuffs 70 excluding the regions 73 on the lengthwise end sides of the leak-preventive cuffs 70 rise from the topsheet 20 and prevent the excreted urine from leaking at a widthwise positions of the absorbent article 1. The leak-preventive cuffs 70 need not be disposed over the entire length of the absorbent article 1 and may be sufficient if they are disposed at least across from the crotch region 13 to the rear waist region 12.

As shown in FIG. 1, in the state of the elastic body 72 being not contracted, that is, in the state of the leak-preventive cuffs 70 being extended, each widthwise edge part 66 of the absorbent sheet 60 is located on the widthwise outer side relative to each free end parts 75 of the leak-preventive cuffs 70. When the absorbent article 1 is worn by a wearer, the leak-prevent cuffs 70 fall on the topsheet 20 and the widthwise outer sides of both edge parts 66 in the width direction of the absorbent sheet 60 are covered with the leak-preventive cuffs 70. Thanks to the presence of the leak-preventive cuffs 70 with low liquid permeability, even when urine seeps from the absorption body 40, the urine can be prevented from contacting with the skin. In the region where the absorbent sheet 60 and the leak-preventive cuffs 70 are overlapped, even when urine seeps from the absorbent sheet 60, the leak-preventive cuffs 70 can be prevented from contacting with the skin. Particularly, in the region 73 on the longitudinal end sides of the leak-preventive cuffs 70, the leak-preventive cuffs 70 are adhered to the topsheet 20 or the backsheet 30 by using an adhesive and therefore, can be fixed so that both edge parts 66 of the absorbent sheet 60 can unfailingly overlap with the leak-preventive cuffs 70. This configuration also increases the effect of not allowing urine seeping from the absorption body 40 due to the body pressure imposed on the later-described absorbent sheet 60 to reach the wearer's skin and the effect of absorbing urine diffused by running down the wearer's skin.

Absorption of the excreted urine by the absorption article 1 in one embodiment of the present invention is described below by referring to the drawings.

Figure 5:
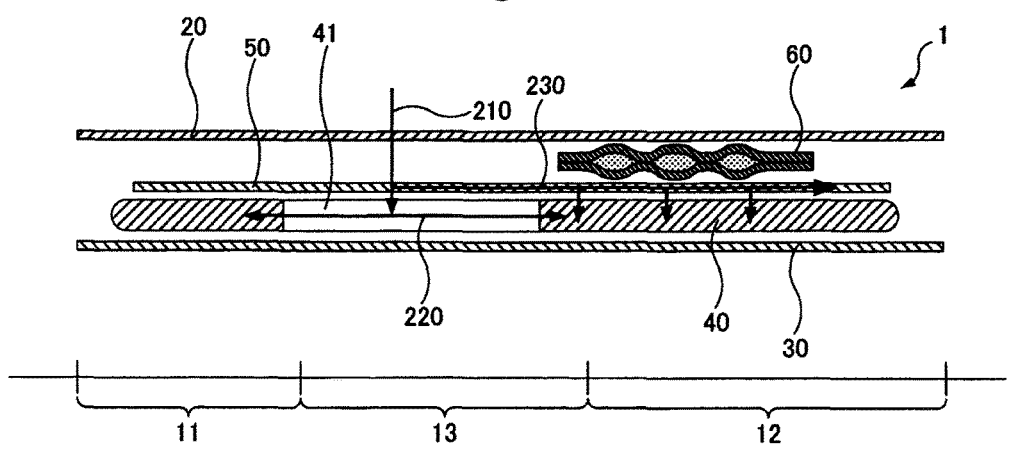
FIG. 5 is a view for explaining absorption of the excreted urine with the absorbent article according to one embodiment of the present invention when the wearer's urination orifice is contacted with the absorbent article.

In the case where the wearer's urination orifice is contacted with the absorbent article 1, as shown in FIG. 5, the excreted urine passes (arrow 210) through the topsheet 20 and the second sheet 50 at a portion of the crotch region 13, where the absorbent sheet 60 is not disposed, and reaches the absorption body 40. The urine reached the absorption body 40 is absorbed from the second sheet 50 side surface of the absorption body 40. Some urine reached (arrow 210) the penetration part 41 of the absorption body 40 is absorbed (arrow 220) from the side wall of the penetration part 41, and some urine reached the compressed groove 42 of the absorption body 40 is absorbed from the side wall of the compressed groove 42. By providing the penetration part 41 and/or the compressed groove 42 in the absorption body 40, the excreted urine is allowed to readily move in the longitudinal direction and therefore, diffusion of the excreted urine to the absorption body 40 is accelerated. Also, a part of the excreted urine diffuses (arrow 230) in the second sheet 50 after passing through the topsheet 20 and is absorbed by the absorption body 40. By allowing the excreted urine to diffuse in the second sheet 50, the excreted urine widely spreads on the second sheet 50 side surface of the absorption body 40. In turn, the area of the absorption body 40 surface for absorbing the excreted urine is increased and therefore, diffusion of the excreted urine to the absorption body 40 is accelerated.

The second sheet 50 is disposed on the side opposite the wearer side of the absorbent sheet 60 and this makes it difficult for the urine diffused in the second sheet 50 to reach the wearer's skin side due to the absorbent sheet 60. Because, when the wearer lies on his (her) back and body pressure is imposed on the rear waist region 12 of the absorbent article 1 from the wearer's buttocks, the urine absorbed in the absorption body 40 seeps but the seeped urine hardly reaches the wearer's skin side due to the absorbent sheet 60. On the other hand, in the region of the crotch region 13, where the absorbent sheet 60 is not disposed, and the front waist region 11, a pressure is less likely to be imposed on the absorbent article 1 and it is lessened that the urine diffused in the second sheet 50 reaches the wearer's skin or the urine absorbed by the absorption body 40 seeps from the absorption body 40. In turn, the skin near the wearer's buttocks is kept dry and comfortable even after the urine is excreted, and the wearer's skin can be protected against irritation due to the excreted urine.

Figure 6:
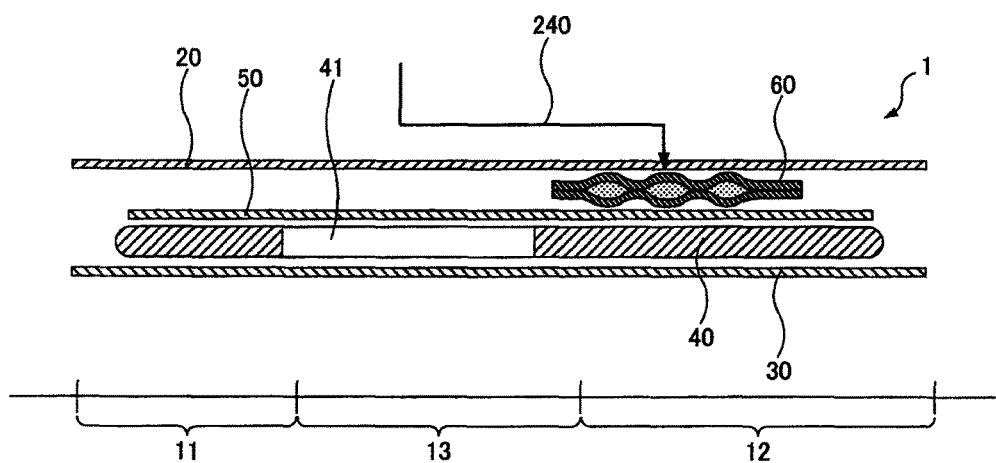
FIG. 6 is a view for explaining absorption of the excreted urine with the absorbent article according to one embodiment of the present invention when the wearer's urination orifice is not contacted with the absorbent article.

In the case where the wearer's urination orifice is not contacted with the absorbent article 1, for example, when the wearer lies on his (her) back, as shown in FIG. 6, the excreted urine runs down the wearer's skin to reach the topsheet 20 in the portion of the crotch region 13 and/or the rear waist region 12, where the absorbent sheet 60 is disposed (arrow 240). The urine reached the topsheet 20 is absorbed by the absorbent sheet 60. Also, as described above, the absorbent polymer has a property of not releasing the once absorbed water even upon application of some pressure and therefore, even when the wearer lies on his (her) back and a body pressure is imposed on the rear waist region 12 of the absorbent article 1 from the wearer's buttocks, the urine absorbed by the absorbent sheet 60 is less likely to seep from the absorbent sheet 60 due to the body pressure. In turn, the wearer's skin is kept dry and comfortable even after the urine is excreted, and the wearer's skin can be protected against irritation from the excreted urine.

The above-described absorbent article 1 in one embodiment can be modified as follows.

(1) In the above-described absorbent article 1 according to one embodiment, at the widthwise central position of the absorption body 40, a penetration part 41 longitudinally extending across the crotch region 13 is provided in the absorption body 40, but in place of the penetration part 41, a thin part where the absorption body 40 is dented from the topsheet 20 side surface of the absorption body 40 and thereby reduced in the thickness may be provided. For example, the thin part of the absorption body can be formed by embossing the absorption body.

Figure 9:
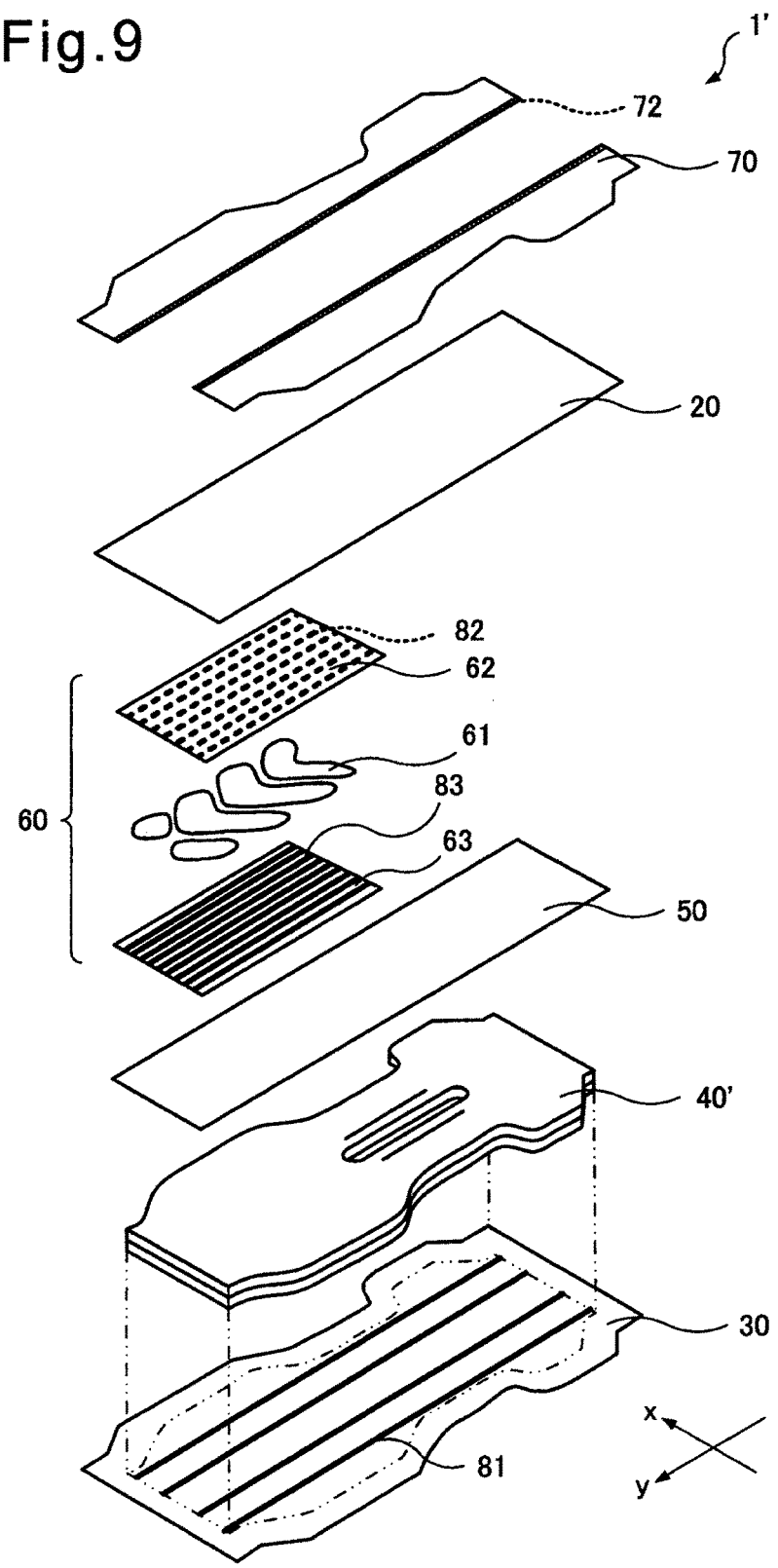
FIG. 9 is an exploded view of a modification example of the absorbent article according to one embodiment of the present invention.

(2) In the above-described absorbent article 1 according to one embodiment, one absorption body 40 is disposed in the absorbent article 1, but two or more absorption bodies may be disposed in the absorbent article. For example, as shown in FIG. 9, in place of the absorption body 40, a stack 40' prepared by stacking two absorption bodies in the thickness direction may be disposed in the absorbent article 1'. Also, in this case, out of two absorption bodies, the penetration part or groove part may be provided only in the absorption body on the second sheet side or only in the absorption body on the topsheet side.

(3) The penetration part and/or groove part of the absorption body may be designed to longitudinally extend even into the region of the absorption body, where the absorbent sheet 60 is disposed. Thanks to this configuration, the excreted urine can rapidly move to the lower side of the absorbent sheet 60 and therefore, a larger amount of urine absorbed by the absorption body 40 is less likely to reach the wearer's skin side due to the absorbent sheet 60.

(4) Out of two liquid-pervious sheets 62, 63 sandwiching an absorbent polymer 61 therebetween in the absorbent sheet 60, the permeability of the liquid-pervious sheet 63 on the second sheet 50 side may be made to be smaller than the permeability of the second sheet 50. Thanks to this configuration, when the wearer lies on his (her) back and a body pressure is imposed on the rear waist region 12 of the absorbent article 1 from the wearer's buttocks, the urine seeped from the absorption body 40 is less likely to pass through the absorbent sheet 60 due to the liquid-pervious sheet 63 of the absorbent sheet 60 and hardly reaches the wearer's skin. For example, a hydrophilic SMS nonwoven fabric may be used for the liquid-pervious sheet 63 on the second sheet 50 side of the absorbent sheet 60. The SMS nonwoven fabric has a melt-blown layer formed by spraying with a spray between two spunbond layers and therefore, this nonwoven fabric is reduced in the fiber interstices and little permeable to liquid and in turn, is suitable for the liquid-pervious sheet 63 on the second sheet 50 side of the absorbent sheet 60. Other than the SMS nonwoven fabric, a nonwoven fabric reduced in the hydrophilicity of the hydrophilic spunbond nonwoven fabric by reducing the amount of the oil solution added at the production of the nonwoven fabric to be from 50 to 60% of the normal amount may be also used. Furthermore, a spunbond nonwoven fabric or point bond nonwoven fabric having a high basis weight (for example, a basis weight of 25 to 35 g/m$^2$) may be also used. As the basis weight is higher, the nonwoven fabric is more reduced in the fiber interstices and becomes less permeable.

Figure 7:
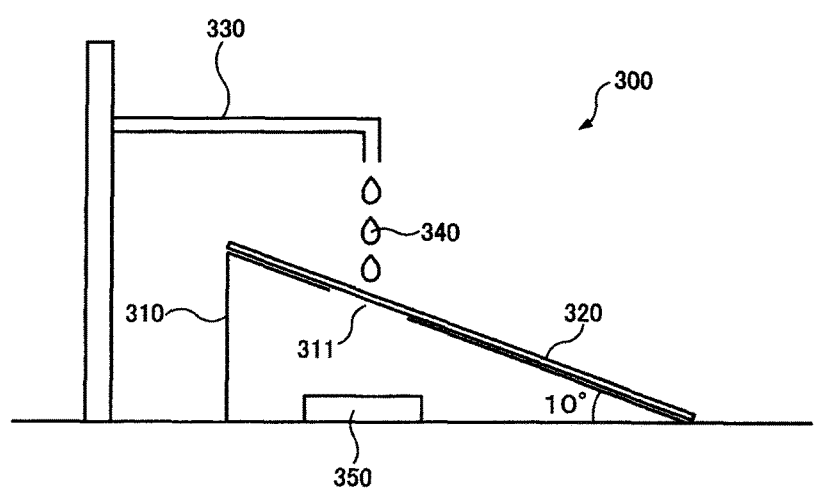
FIG. 7 is a view for explaining the method for evaluating the permeability of the liquid-pervious sheet.

The permeability of the liquid-pervious sheet can be evaluated, for example, by using the permeability evaluation apparatus 300 shown in FIG. 7. The evaluation of permeability by the permeability evaluation apparatus 300 is performed as follows.

(i) A liquid-pervious sheet 320 is placed on a sample stage 310 having a gradient of 10°. A circular hole 311 with a diameter of 65 mm is provided in the sample stage 310 surface where the liquid-pervious sheet 320 is placed.

(ii) Using a tube 330 with a diameter of 5 mm, 25 ml of artificial urine 340 is dropped from the height of 80 mm over 3.75 seconds. The dropped artificial urine 340 permeates the liquid-pervious sheet 320, passes through the hole 311 of the sample stage 310, and falls in a recovery dish 350.

(iii) The weight of the artificial urine collected in the recovery dish 350 is measured.

(iv) The percentage permeation is calculated according to the following formula:

Percentage permeation (%)=weight (g) of artificial urine collected in the recovery dish/25 (g)×100

A liquid-pervious sheet having a high percentage permeation is high in the permeability, and a liquid-pervious sheet having a low percentage permeation is low in the permeability. This permeability test is proposed for this application.

The results of evaluation of the permeability by the permeability evaluation apparatus 300 are shown in Table 1.

TABLE 1

Percentage Permeation of Nonwoven Fabric

| | Nonwoven Fabric | Basis Weight (g/m$^2$) | Weight of Recovery Dish Before Measurement (g) | Weight of Recovery Dish After Measurement (g) | Weight of Artificial Urine Collected in Recovery Dish (g) | Percentage Permeation (%) |
|---|---|---|---|---|---|---|
| 1 | Hydrophobic SMS nonwoven fabric | 15 | 18.98 | 18.98 | 0.00 | 0 |
| 2 | Hydrophilic tissue | 15 | 18.98 | 42.21 | 23.23 | 93 |
| 3 | Hydrophilic spunbond nonwoven fabric | 20 | 18.98 | 41.88 | 22.90 | 92 |
| 4 | Hydrophilic SMS nonwoven fabric | 10 | 18.98 | 38.44 | 19.46 | 78 |
| 5 | Hydrophilic air-through nonwoven fabric | 25 | 18.98 | 43.01 | 24.03 | 96 |
| 6 | Hydrophilic point bond nonwoven fabric | 23 | 18.98 | 30.84 | 11.86 | 47 |

TABLE 1-continued

Percentage Permeation of Nonwoven Fabric

| | Nonwoven Fabric | Basis Weight ($g/m^2$) | Weight of Recovery Dish Before Measurement (g) | Weight of Recovery Dish After Measurement (g) | Weight of Artificial Urine Collected in Recovery Dish (g) | Percentage Permeation (%) |
|---|---|---|---|---|---|---|
| 7 | Hydrophilic spun lace nonwoven fabric | 38 | 18.98 | 35.08 | 16.10 | 64 |

It is seen from these results that when tissue having a basis weight of 15 $g/m^2$ is used for the second sheet 50, a hydrophilic SMS nonwoven fabric having a basis weight of 10 $g/m^2$, a hydrophilic point bond nonwoven fabric having a basis weight of 23 $g/m^2$, or a spun lace nonwoven fabric having a basis weight of 38 $g/m^2$ is suitable for the liquid-pervious sheet 63 on the second sheet 50 side. Also, it is seen that in the case where a spun lace nonwoven fabric having a basis weight of 38 $g/m^2$ is used for the second sheet 50, a hydrophilic point bond nonwoven fabric having a basis weight of 23 $g/m^2$ is suitable for the liquid-pervious sheet 63 on the second sheet 50 side.

(5) In the case of providing a colored streaky adhesive part 82 on the liquid-pervious sheets 62, 63 of the absorbent sheet 60, the amount of the adhesive coated may be reduced in the widthwise center of the absorbent sheet 60. For example, the adhesive may not be coated on the widthwise center of the absorbent sheet 60. By taking notice of the region where the colored adhesive part 82 is not provided, it is easy to recognize the widthwise center (centerline) of the absorbent article.

Figure 8:
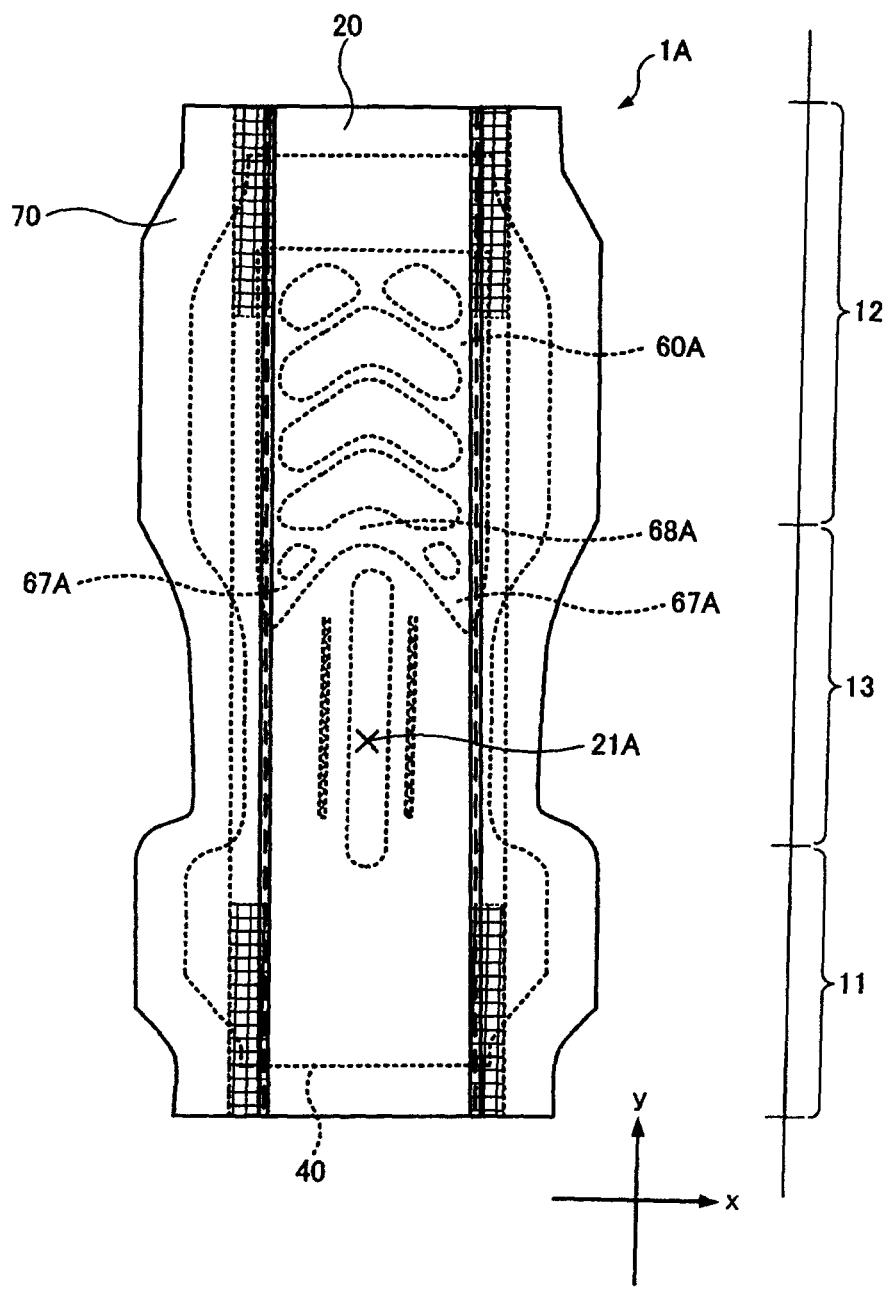
FIG. 8 is a view showing a modification example of the absorbent article according to one embodiment of the present invention.

(6) As in the absorbent article 1A shown in FIG. 8, the widthwise outside region 67A present on both sides of the widthwise central region 68A of the absorbent sheet 60A may be designed to extend toward the front waist region 11 side ahead of the widthwise central region 68A of the absorbent sheet 60A. In this case, an absorbent polymer-existing region is disposed in the region 67A extending ahead of the widthwise central region 68A of the absorbent sheet 60A. Thanks to this configuration, urine can be absorbed also in the region 67A extending ahead of the widthwise central region 68A of the absorbent sheet 60A. In the case where the wearer's urination orifice is contacted with the absorbent article 1, the urine excreted is preferably absorbed by the absorption body 40 as much as possible. Accordingly, when the wearer's urination orifice is contacted with the absorbent article 1, in order to allow the excreted urine to flow on the topsheet and be less absorbed directly by the absorbent sheet 60, the absorbent sheet 60 is preferably somewhat away from the point at which the wearer's urination orifice contacts with the absorbent article 1. On the other hand, in order to prevent the urine seeped from the absorption body 40 due to a wearer's body pressure from reaching the wearer's skin, the area of the absorbent sheet 60 is preferably wider. As in the absorbent article 1A shown in FIG. 8, when the region 67A on both widthwise end sides of the absorbent sheet 60A extends toward the front waist region 11 side ahead of the widthwise central region 68A of the absorbent sheet 60A, the area of the absorbent sheet 60A can be made wide while keeping the distance between the absorbent sheet 60A and the point 21A at which the wearer's urination orifice contacts with the absorbent article 1.

The present invention is not limited to the urine-absorbing pad. The present invention may be, for example, an absorbent article such as disposable diaper, toilet training pant and incontinence brief.

It is also possible to combine the embodiment with one modification example or a plurality of modification examples. Modification examples may be also combined with each other in any combination.

The descriptions in the foregoing pages are absolutely one example, and the invention is not limited to the above-described embodiments by any means.

Examples

The present invention is described in greater detail below by referring to non-limiting Examples. However, the present invention is not limited to the following Examples.

Using the following sample and test method, it was confirmed that when the wearer's urination orifice is contacted with the absorbent article and when the wearer's urination orifice is not contacted with the absorbent article, the excreted urine is not allowed to seep from the absorbent article and wet the wearer's buttocks (rewet).

Sample

A rewet test was performed using an absorbent article having the following constituent elements.

Topsheet: A hydrophilic spunbond nonwoven fabric having a basis weight of 20 $g/m^2$.

Absorption body: A stack obtained by stacking an upper-layer absorption body composed of a pulp having a basis weight of 220 $g/m^2$ and an absorbent polymer having a basis weight of 82 $g/m^2$ on a lower-layer absorption body composed of a pulp having a basis weight of 180 $g/m^2$ and an absorbent polymer having a basis weight of 33 $g/m^2$ (water retention amount: 450 g).

Absorbent sheet: A sheet obtained by sandwiching 2 g of an absorbent polymer between hydrophilic spunbond nonwoven fabrics each having a basis weight of 20 $g/m^2$ and joining the nonwoven fabrics together.

Second sheet: A tissue having a basis weight of 15 $g/m^2$.

Test Method 80 ml of artificial urine is charged to the absorbent article every 5 minutes. This operation is performed 5 times. That is, 400 ml of artificial urine is charged. The artificial urine is an aqueous solution prepared by dissolving 200 g of urea, 80 g of sodium chloride, 80 g of magnesium sulfate, 8 g of calcium chloride and about 1 g of a dye: Blue No. 1, in 10 liters of ion-exchanged water. At 5 minutes after charging 400 ml of artificial urine, a filter paper of 70 g (100 mm×100 mm) is placed on the rewet measurement position, a weight of 3.5 kg with the bottom surface having a size of 100 mm×100 mm is placed thereon, and the artificial urine seeping from the absorbent article is absorbed by the filter paper. The weight of the filter paper before absorbing the artificial urine is subtracted from the weight of the filtration paper having absorbed therein the artificial urine, whereby the amount of the seeped artificial urine, i.e., the rewet amount, is calculated. An adsorbent article from which the absorbent sheet is removed is also tested in the same manner. A smaller rewet amount indicates that the excreted urine is less likely to seep from the absorbent article 1 and wet the wearer's buttocks. The test was carried out at a temperature of 20° C. and a relative humidity of 60%. The filter paper is a qualitative filter paper for mid-grade filtration, manufactured by Advantec Toyo Kaisha, Ltd, the grade of which is No. 2. The No. 2 grade filter paper corresponds to a type-II filter paper defined in JIS P 3801.

Results

When the artificial urine is charged to the position at which the wearer's urination orifice is contacted with the absorbent article, the rewet amount in the portion where the absorbent sheet is disposed was 0.1 g. The same test was performed by removing the absorbent sheet from the absorbent article, as a result, the rewet amount was increased to 1.0 g. As confirmed by this result, the problem that when the wearer's urination orifice is contacted with the absorbed article, the excreted urine seeps from the absorbent article to wet the wearer's buttocks could be improved by disposing an absorbent sheet.

In the case where the wearer's urination orifice is not contacted with the absorbent article, when artificial urine was charged to the topsheet in the region allowing the excreted urine to seep in by running down the wearer's skin, i.e., the topsheet in the region having disposed therein the absorbent sheet, the rewet amount in the portion where the absorbent sheet was disposed was 39 g. The same test was performed by removing the absorbent sheet from the same absorbent article, as a result, the artificial urine seeped from the absorption body and the rewet amount was increased to 72 g. As confirmed by this result, the problem that when the wearer's urination orifice is not contacted with the absorbed article 1, the excreted urine, after being absorbed by the absorbent article, seeps from the absorbent article to wet the wearer's buttocks could be improved by disposing an absorbent sheet.

DESCRIPTION OF NUMERICAL REFERENCES 1, 1A Absorbent article
20 Topsheet
30 Backsheet
40 Absorption body
41 Penetration part
42 Compressed groove
50 Second sheet
60, 60A Absorbent sheet
61 Absorbent polymer
62, 63 Liquid-pervious sheet
64 Absorbent polymer-existing region
65 Absorbent polymer-nonexisting region
66 Edge part
70 Leak-preventive cuff
71 Edge part
72 Elastic body
300 Permeability evaluation apparatus

The invention claimed is:

1. An absorbent article having a front waist region, a rear waist region and a crotch region located between the front and rear regions in a longitudinal direction from a front side to a rear side, comprising:
   a liquid-pervious topsheet, a backsheet,
   an absorption body intervening between said topsheet and said backsheet, the absorption body having a longitudinally extending penetration part in at least a part of said crotch region,
   a second sheet disposed between said absorption body and said topsheet, and
   an absorbent sheet between said top sheet and said second sheet, comprising at least one liquid-pervious sheet having sandwiched thereby an absorbent polymer,
   wherein:
   said second sheet is formed from tissue, point bond nonwoven fabric and rayon-containing spun lace nonwoven fabric or a mixture thereof, and is higher in the liquid diffusibility than said topsheet,
   said topsheet, said backsheet, said absorption body and said second sheet are disposed across said front waist region, said crotch region and said rear waist region, and
   said absorbent sheet is disposed in at least a part of said rear waist region and does not extend entirely across the crotch region, and in which
   when a liquid is applied to said absorbent article, some liquid which reaches the penetration part of said absorption body is absorbed from the side wall of the penetration part, and thus the liquid is allowed to readily moved in the longitudinal direction of said absorption body.

2. The absorbent article as claimed in claim 1, wherein said at least one liquid-pervious sheet is a folded liquid-pervious sheet or two liquid-pervious sheets.

3. The absorbent article as claimed in claim 2, wherein said absorbent sheet has an absorbent polymer-existing region in which said absorbent polymer is sandwiched by said at least one liquid-pervious sheet and an absorbent polymer-nonexisting region in which said absorbent polymer is not sandwiched between said two liquid-pervious sheets.

4. The absorbent article as claimed in claim 3, wherein the widthwise central portion in said absorbent polymer-existing region is located on the rear side in a direction towards the edge of the rear waist region compared with each of widthwise outward portions relative to said widthwise central portion in said absorbent polymer-existing region.

5. The absorbent article as claimed in claim 4, wherein:
   a plurality of adhesive parts extending in the longitudinal direction of said absorbent article and aligning in the width direction of said absorbent article are provided on each of said liquid-pervious sheet surfaces sandwiching said absorbent polymer therebetween in said absorbent sheet, and
   the adhesive part-to-adhesive part distance between adjacent adhesive parts of the adhesive parts provided on the liquid-pervious sheet on the second sheet side in said absorbent sheet is small compared with the adhesive part-to-adhesive part distance of the adhesive parts provided on the liquid-pervious sheet on the topsheet side in said absorbent sheet.

6. The absorbent article as claimed in claim 3, wherein:
   a plurality of adhesive parts extending in the longitudinal direction of said absorbent article and aligning in the width direction of said absorbent article are provided on each of said liquid-pervious sheet surfaces sandwiching said absorbent polymer therebetween in said absorbent sheet, and the adhesive part-to-adhesive part distance between adjacent adhesive parts of the adhesive parts provided on the liquid-pervious sheet on the second sheet side in said absorbent sheet is small compared with the adhesive part-to-adhesive part distance of the adhesive parts provided on the liquid-pervious sheet on the topsheet side in said absorbent sheet.

7. The absorbent article as claimed in claim 2, wherein:
a plurality of adhesive parts extending in the longitudinal direction of said absorbent article and aligning in the width direction of said absorbent article are provided on each of said liquid-pervious sheet surfaces sandwiching said absorbent polymer therebetween in said absorbent sheet, and the adhesive part-to-adhesive part distance between adjacent adhesive parts of the adhesive parts provided on the liquid-pervious sheet on the second sheet side in said absorbent sheet is small compared with the adhesive part-to-adhesive part distance of the adhesive parts provided on the liquid-pervious sheet on the topsheet side in said absorbent sheet.

8. The absorbent article as claimed in claim 1, wherein said absorbent sheet has an absorbent polymer-existing region in which said absorbent polymer is sandwiched by said at least one liquid-pervious sheet and an absorbent polymer-nonexisting region in which said absorbent polymer is not sandwiched between said two liquid-pervious sheets.

9. The absorbent article as claimed in claim 8, wherein:
a plurality of adhesive parts extending in the longitudinal direction of said absorbent article and aligning in the width direction of said absorbent article are provided on each of said liquid-pervious sheet surfaces sandwiching said absorbent polymer therebetween in said absorbent sheet, and the adhesive part-to-adhesive part distance between adjacent adhesive parts of the adhesive parts provided on the liquid-pervious sheet on the second sheet side in said absorbent sheet is small compared with the adhesive part-to-adhesive part distance of the adhesive parts provided on the liquid-pervious sheet on the topsheet side in said absorbent sheet.

10. The absorbent article as claimed in claim 8, wherein the widthwise central portion in said absorbent polymer-existing region is located on the rear side in a direction towards the edge of the rear waist region compared with each of widthwise outward portions relative to said widthwise central portion in said absorbent polymer-existing region.

11. The absorbent article as claimed in claim 10, wherein:
a plurality of adhesive parts extending in the longitudinal direction of said absorbent article and aligning in the width direction of said absorbent article are provided on each of said liquid-pervious sheet surfaces sandwiching said absorbent polymer therebetween in said absorbent sheet, and the adhesive part-to-adhesive part distance between adjacent adhesive parts of the adhesive parts provided on the liquid-pervious sheet on the second sheet side in said absorbent sheet is small compared with the adhesive part-to-adhesive part distance of the adhesive parts provided on the liquid-pervious sheet on the topsheet side in said absorbent sheet.

12. The absorbent article as claimed in claim 1, wherein:
a plurality of adhesive parts extending in the longitudinal direction of said absorbent article and aligning in the width direction of said absorbent article are provided on each of said liquid-pervious sheet surfaces sandwiching said absorbent polymer therebetween in said absorbent sheet, and the adhesive part-to-adhesive part distance between adjacent adhesive parts of the adhesive parts provided on the liquid-pervious sheet on the second sheet side in said absorbent sheet is small compared with the adhesive part-to-adhesive part distance of the adhesive parts provided on the liquid-pervious sheet on the topsheet side in said absorbent sheet.

13. The absorbent article as claimed in claim 12, wherein the adhesive is not coated on the widthwise center of the absorbent sheet.

14. The absorbent article as claimed in claim 1, wherein said absorption body has a longitudinally extending groove part in at least a part of said crotch region.

15. The absorbent article as claimed in claim 1, wherein said penetration part of said absorption body longitudinally extends into a region in which said absorbent sheet of said absorption body is disposed.

16. The absorbent article as claimed in claim 1, wherein the permeability of the liquid-pervious sheet of said absorbent sheet on the second sheet side is smaller than the permeability of said second sheet.

17. The absorbent article as claimed in claim 1, wherein:
longitudinally extending leak-preventive cuffs are disposed in both widthwise side parts of said absorbent article,
said leak-preventive cuffs have a base end part joined with the widthwise side parts of said absorbent article and an unjoined free end parts,
said free end parts are located on the widthwise inner sides of said absorbent article relative to said base end part,
an elastic bodies capable of extending in the longitudinal direction and fixed in an extended state are provided in the vicinity of said free end parts, such that in a state of said leak-preventive cuffs being extended, each widthwise end part of said absorbent sheet is located on the widthwise outer sides than each free end part of said leak-preventive cuffs.

18. The absorbent article as claimed in claim 1, wherein:
said absorbent sheet has a widthwise central region and a widthwise outside region present on both sides of said widthwise central region, and
said widthwise outside region is more extending to said front waist region side than said widthwise central region.

19. The absorbent article as claimed in claim 1, wherein:
the percentage of the area of the absorbent polymer-existing regions to the area of the absorbent sheet is 40 to 80%.

20. The absorbent article as claimed in claim 1, wherein:
the absorption body consists of a stack prepared by stacking two absorption bodies in the thickness direction.

21. The absorbent article as claimed in claim 1, wherein the second sheet is in contact with said absorbent sheet in said rear waist region, and is in contact with said topsheet disposed across said front waist region in said crotch region.

* * * * *